US012596120B2

(12) United States Patent
Schlothauer et al.

(10) Patent No.: US 12,596,120 B2
(45) Date of Patent: Apr. 7, 2026

(54) PH-GRADIENT SPR-BASED BINDING ASSAY

(71) Applicant: Hoffmann-La Roche Inc., Little Falls, NJ (US)

(72) Inventors: Tilman Schlothauer, Penzberg (DE); Christian Spick, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1113 days.

(21) Appl. No.: 17/362,406

(22) Filed: Jun. 29, 2021

(65) Prior Publication Data

US 2021/0325385 A1    Oct. 21, 2021

Related U.S. Application Data

(63) Continuation of application No. PCT/EP2019/086740, filed on Dec. 20, 2019.

(30) Foreign Application Priority Data

Dec. 30, 2018    (EP) ..................................... 18215921

(51) Int. Cl.
*G01N 33/557* (2006.01)
*G01N 33/543* (2006.01)

(52) U.S. Cl.
CPC ......... *G01N 33/557* (2013.01); *G01N 33/543* (2013.01)

(58) Field of Classification Search
CPC ............................ G01N 33/543; G01N 33/557
See application file for complete search history.

(56) References Cited

U.S. PATENT DOCUMENTS

| | | | |
|---|---|---|---|
| 8,906,672 B2 † | 12/2014 | Quinn | |
| 2005/0019933 A1 | 1/2005 | Andersson et al. | |
| 2010/0256338 A1 | 10/2010 | Brinkmann et al. | |
| 2011/0111406 A1 | 5/2011 | Igawa et al. | |
| 2011/0295512 A1 | 12/2011 | Qinn | |
| 2017/0227547 A1 | 8/2017 | Emrich et al. | |

FOREIGN PATENT DOCUMENTS

| | | |
|---|---|---|
| CN | 102132143 | 7/2011 |
| CN | 102844332 | 12/2012 |
| CN | 105829889 A | 8/2016 |
| CN | 106103478 A | 11/2016 |
| EP | 2275443 A1 | 1/2011 |
| JP | 2013-500244 A | 1/2013 |
| JP | 2017-507907 A | 3/2017 |
| WO | 2009/025680 A1 | 2/2009 |
| WO | 2010/022910 A1 | 3/2010 |
| WO | 2011/009623 A1 | 1/2011 |
| WO | 2011/111007 A2 | 9/2011 |
| WO | 2012/023053 A2 | 2/2012 |
| WO | 2013/120929 A1 | 8/2013 |
| WO | 2015/086549 A1 | 6/2015 |
| WO | 2015/135884 | 9/2015 |
| WO | 2015/140126 A1 | 9/2015 |
| WO | 2015/172800 A1 | 11/2015 |

OTHER PUBLICATIONS

Cymer et al., "Evaluation of an FcRn affinity chromatographic method for IgG1-type antibodies and evaluation of IgG variants" Bioanalysis 9(17):1305-1317 ( 2017).
Fekete, S., et al., "Method development for the separation of monoclonal antibody charge variants in cation exchange chromatography, Part II: pH gradient approach" J Pharm Biomed Anal 102:282-289 (Jan. 5, 2015).
Hearty et al., "Measuring Antibody-Antigen Binding Kinetics Using Surface Plasmon Resonance" Methods in Molecular Biology 907:pp. 411-442 ( 2012).
Igawa, T., et al., "Antibody recycling by engineered pH-dependent antigen binding improves the duration of antigen neutralization" Nat Biotechnol 28(11):1203-1207 (Nov. 1, 2010).
"International Preliminary Report on Patentability—PCT/EP2019/086740" (Report Issuance Date: Jun. 16, 2021; Chapter I),:pp. 1-7 (Jul. 15, 2021).
"International Search Report—PCT/EP2019/086740" (w/Written Opinion),:pp. 1-12 (Jan. 23, 2020).
Lakayan, D., et al., "Affinity profiling of monoclonal antibody and antibody-drug-conjugate, preparations by coupled liquid chromatography-surface plasmon resonance biosensing" Anal Bioanal Chem 410(30):7837-7848 (Oct. 17, 2018).
Li et al., "Effect of antigen attenuation of G145R mutation recombinant HBsAg to affinity chromatography" Biotechnology (including English abstract),(5):52-54 ( 2009).
Lingg, N., et al., "Highly linear pH gradients for analyzing monoclonal antibody charge heterogeneity in the alkaline range" J Chromatogr A 1319:65-71 (Dec. 6, 2013).
Meschendoerfer, W., et al., "SPR-based assays enable the full functional analysis of bi-specific molecules" J Pharm Biomed Anal 132:141-147 (Jan. 5, 2017).
Naik et al., "Monitoring the Kinetics of the pH-Driven Transition of the Anthrax Toxin Prepore to the Pore by Biolayer Interferometry and Surface Plasmon Resonance" Biochemistry 52(37):pp. 6335-6347 (Aug. 21, 2013).
Raghavan, M. et al., "Analysis of the pH dependence of the neonatal Fc receptor/immunoglobulin G interaction using antibody and receptor variants" ACS Biochemistry 34(45):14649-14657 (Nov. 14, 1995).

(Continued)

*Primary Examiner* — Galina M. Yakovleva
(74) *Attorney, Agent, or Firm* — Nicole M. Fortuné

(57) ABSTRACT

Herein is reported a method for determining the dissociation rate constant $k_d$ of an antibody from its antigen at the dissociation pH-value, wherein the method comprises the steps of immobilizing at a first pH-value the antibody on a solid phase to which the antigen of the antibody has been conjugated; applying a pH-gradient from the first pH-value to the dissociation pH-value and thereafter maintaining the pH-value at said dissociation pH-value; and recording the binding signal during the maintaining of the pH-value and calculating therefrom the dissociation rate constant $k_d$ of the antibody from its antigen at the dissociation pH-value.

7 Claims, 3 Drawing Sheets

(56)                          References Cited

OTHER PUBLICATIONS

Schasfoort, R., Handbook of Surface Plasmon Resonance "Chapter 12: Future Trends in SPR Technology" Schasfoort, Richard BM . . . ed, 2nd edition, London-GB:Royal Society of Chemistry,:354-394 (Dec. 31, 2008).

Schlothauer, T., et al., "Analytical FcRn affinity chromatography for functional characterization of monoclonal antibodies" MABS 5(4):576-586 (Jul. 1, 2013).

Shank-Retzlaff, M., et al., "Analyte Gradient-Surface Plasmon Resonance: A One-Step Method for Determining Kinetic Rates and Macromolecular Binding Affinities" Anal Chem 72(17):4212-4220 (Sep. 1, 2000).

Watanabe et al., "Optimizing pH Response of Affinity between Protein G and IgG Fc" The Journal of Biological Chemistry 284(18):12373-12383 (May 1, 2009).

Yanhua Fan, "Studies on the interaction between biomolecules by surface plasmon resonance technology and fluorescence spectrometry" Chinese Master's Theses, Shanxi University (English abstract on pp. 13-14 of PDF),(6):1-84 ( 2011).

De Mol et al., "Surface Plasmon Resonance" Methods in Molecular Biology: 1-287 ( 2010).

Isakova et al., "The Ultrathin Polymer Films Based on Polyaniline as SPR Sensitive Diagnostic Systems" Nanocon (Oct. 14-15, 2015).

Maxfield et al., "Endosome Acidification and the Pathways of Receptor-Mediated Endocytosis" Advances In Experimental Medicine and Biology 225:189-189 ( 1987).

Schuck et al., "Kinetics of Ligand Binding to Receptor Immobilized in a Polymer Matrix, as Detected with an Evanescent Wave Biosensor. I. A Computer Simulation of the Influence of Mass Transport" Biophysical Journal vol. 70:1230-1249 ( 1996).

Tang et al., "Nonregeneration Protocol for Surface Plasmon Resonance: Study of High-Affinity Interaction with High-Density Biosensors" Analytical Chemistry vol. 78(No. 6):1841-1848 (Mar. 15, 2006).

Wang et al., "Investigation of endosome and lysosome biology by ultra pH-sensitive nanoprobes" Advanced Drug Delivery Reviews vol. 113:87-96 ( 2017).

Screenshots providing evidence of the webinar of Dec. 11, 2018 by Phillip Page and Mary Murphy, titled "Combining Reichert's SPR Systems With Other Informative Techniques".

Transcript of webinar of Dec. 11, 2018 by Phillip Page and Mary Murphy, titled "Combining Reichert's SPR Systems With Other Informative Techniques".

Slides of webinar of Dec. 11, 2018 by Phillip Page and Mary Murphy, titled "Combining Reichert's SPR Systems With Other Informative Techniques".

Evidence of publication date of Dec. 11, 2018 by Phillip Page and Mary Murphy, titled "Combining Reichert's SPR Systems With Other Informative Techniques"—Youtube screenshot.

"Information regarding Labroots webinars—Screenshot", Jan. 31, 2025.

"Wayback machine entry for Information regarding Labroots webinars" Jan. 31, 2025.

Danlin Yang et al., Maximizing in vivo Target Clearance by Design of pH-Dependent Target Binding Antibodies with Altered Affinity to FcRn, 9 MABS 1105-1117 (Sep. 18, 2017).†

Xiangdan Wang et al, Impact of SPR Biosensor Assay Configuration on Antibody: Neonatal Fc Receptor Binding Data, 9 MABS 319-332 (Jan. 9, 2017).†

The Protein Man, Protein Immunoprecipitations: Which Method to Use, The Protein Man's Blog 7 pages (May 14, 2013, 1:40 pm) https://info.gbiosciences.com/blog/bid/179306/protein-immunoprecipitations-which-method-to-use.†

† cited by third party

PH-GRADIENT SPR-BASED BINDING ASSAY

CROSS REFERENCE TO RELATED APPLICATIONS

This application is a continuation of International Application No. PCT/EP2019/086740, filed Dec. 20, 2019, claiming priority to European Application No. 18215921.0, filed Dec. 30, 2018 which are incorporated herein by reference in their entirety.

The current invention is in the field of functional assays. Herein is reported a novel SPR-based binding assay for measuring the pH-dependent interactions of antibodies.

BACKGROUND OF THE INVENTION

SPR (surface plasmon resonance) is a biosensor-based technology to measure real time protein-protein interaction. SPR technology has become a standard tool in biopharmaceutical research and development [1-5], and is commonly employed to determine binding constants for macromolecular interactions. The ability to determine association and dissociation kinetics for molecular interactions provides detailed insights into the mechanism of complex formation [6]. This information is becoming an essential part of the selection and optimization process for monoclonal antibodies and other biopharmaceutical products [7-10]. In addition, SPR technology allows the determination of the binding activity (binding capacity) of e.g. an antibody binding a target.

The antigen-neutralizing capacity of a single antibody molecule depends on its affinity. By increasing the affinity, an antigen can be neutralized by smaller amount of an antibody. Various methods can be used to enhance the antibody affinity. Furthermore, if the affinity could be made infinite by covalently binding the antibody to the antigen, a single antibody molecule could neutralize one antigen molecule (a divalent antibody can neutralize two antigen molecules). However, due to the stoichiometric neutralization of one antibody against one antigen (one divalent antibody against two antigens) it is impossible to completely neutralize antigen with the smaller amount of antibody than the amount of antigen. To prolong the neutralization effect of a neutralizing antibody for a certain period, the antibody must be administered at a dose higher than the amount of antigen produced in the body during the same period. With the improvement of antibody pharmacokinetics or affinity maturation technology alone, there is a limitation in the reduction of the required antibody dose.

Accordingly, in order to sustain antibody's antigen-neutralizing effect for a target period with smaller amount of the antibody than the amount of antigen, a single antibody must neutralize multiple antigens.

Shank-Retzlaff, M. L. and Sligar, S. G. disclosed analyte gradient-surface plasmon resonance as a one-step method for determining kinetic rates and macromolecular binding affinities (Anal. Chem. 72 (2000) 4212-4220).

US 2005/0019933 disclosed a method of characterizing interaction between two species in a liquid environment, wherein a liquid comprising said at least one species is passed as a flow through a measurement system, and wherein the interaction takes place within said measurement system. The method comprises generating a concentration gradient of at least a one of said species or of at least one other species having an influence on the interaction or on interacted components.

Schasfoort, R. B. M., et al. disclosed future trends in SPR technology in the handbook of surface plasmon resonance (31 Dec. 2008 (2008-12-31), pages 354-394, Cambridge.

US 2010/256338 disclosed multispecific, especially bispecific antibodies comprising full length antibodies and single chain Fab fragments, methods for their production, pharmaceutical compositions containing the antibodies, and uses thereof.

WO 2012/023053 disclosed novel bispecific monoclonal antibodies carrying a different specificity for each binding site of the immunoglobulin molecule and methods for producing novel bispecific monoclonal antibodies carrying a different specificity for each binding site of the immunoglobulin molecule.

Schlothauer, T., et al., disclosed analytical FcRn affinity chromatography for functional characterization of monoclonal antibodies (mAbs 5 (2013) 576-586.

WO 2015/140126 disclosed a method for determining the presence of antibody-Fab-FcRn interaction in an antibody-Fc-FcRn complex influencing the in vivo half-life using an FcRn affinity chromatography column with a positive linear pH gradient elution in the presence of different salt concentrations. WO 2015/172800 disclosed novel multispecific molecules and novel treatment methods based on such multispecific molecules.

Meschendoerfer, W. et al., disclosed SPR-based assays enable the full functional analysis of bispecific molecules (J. Pharm. Biomed. Anal. 132 (2016) 141-147).

EP 2 275 443 disclosed methods for improving the pharmacokinetics of antigen-binding molecules and methods for increasing the number of times of antigen-binding of antigen-binding molecules, as well as antigen-binding molecules having improved pharmacokinetics, antigen-binding molecules having increased number of times of antigen-binding, and methods for producing such molecules.

SUMMARY OF THE INVENTION

Herein is reported a novel SPR-based assay for measuring pH-dependent binding activity of antibodies.

One aspect as reported herein is an assay or method for determining if the binding of a (monoclonal) antibody to its antigen is pH-dependent (i.e. the antibody has pH-dependent antigen-binding), wherein the method comprises the following steps:

a) capturing/immobilizing at a first pH-value the antibody on a solid phase to which the antigen of the antibody has been conjugated, i.e. the capturing/immobilization is by interaction of the antibody with its antigen, b) applying a pH-gradient from the first pH-value to a second pH-value to the solid phase and monitoring the dissociation of the antibody from the solid phase, wherein the binding of the antibody to its antigen is pH-dependent if dissociation of the antibody from the solid phase can be detected in step b).

An exemplary SPR sensogram showing a pH-dependent dissociation is shown in FIG. 2.

One aspect as reported herein is an assay or method for selecting a (monoclonal) antibody that binds to its antigen pH-dependent (i.e. the antibody has a pH-dependent antigen-binding), wherein the method comprises the following steps:

a) capturing/immobilizing at a first pH-value the antibody on a solid phase to which the antigen of the antibody has been conjugated, i.e. the capturing/immobilization is by interaction of the antibody with its antigen, b) applying a pH-gradient from the first pH-value to a second pH-value to the solid phase and monitoring the dissociation of the antibody from the solid phase, wherein the antibody is selected if dissociation of the antibody from the solid phase can be detected in step b).

One aspect as reported herein is an assay or method for determining the pH-value at which an antibody that binds to its antigen pH-dependent dissociates from its antigen (pH-dependent dissociation), wherein the method comprises the following steps:

a) capturing/immobilizing at a first pH-value the antibody on a solid phase to which the antigen of the antibody has been conjugated, i.e. the capturing/immobilization is by interaction of the antibody with its antigen, b) applying a pH-gradient from the first pH-value to a second pH-value to the solid phase and monitoring the dissociation of the antibody from the solid phase, wherein the pH-value at which the antibody dissociates from its antigen is the pH-value of the pH-gradient at which dissociation of the antibody from the solid phase can be detected in step b).

One aspect as reported herein is an assay or method for determining the dissociation rate constant $k_d$ of an antibody from its antigen, whereby the antibody binds to its antigen pH-dependent (pH-dependent dissociation), at the dissociation pH-value (the dissociation pH-values is the pH-value at which the dissociation of the antibody from its antigen can be detected), wherein the method comprises the following steps:

a) capturing/immobilizing at a first pH-value the antibody on a solid phase to which the antigen of the antibody has been conjugated, i.e. the capturing/immobilization is by interaction of the antibody with its antigen, b) applying a pH-gradient from the first pH-value to the dissociation pH-value to the solid phase and thereafter maintaining the pH-value at said dissociation pH-value, c) recording the (binding) signal and calculating therefrom the dissociation rate constant $k_d$ and thereby determining the dissociation rate constant $k_d$ at the dissociation pH-value.

An exemplary SPR sensogram showing dissociation at the dissociation pH-value is shown in FIG. 3.

One aspect as reported herein is an assay or method for determining the influence of antibody oligomerization on the pH-dependent binding of a (monoclonal) antibody to its antigen, wherein the method comprises the following steps:

a) capturing/immobilizing at a first pH-value the monomeric antibody on a solid phase to which the antigen of the antibody has been conjugated, i.e. the capturing/immobilization is by interaction of the antibody with its antigen, b) applying a pH-gradient from the first pH-value to a second pH-value to the solid phase, monitoring the dissociation of the antibody from the solid phase, and calculating a dissociation rate therefore, c) repeating steps a) to b) with the dimeric, trimeric, tetrameric and/or oligomeric antibody, wherein the pH-dependent binding of the antibody to its antigen is influenced by oligomerization if the dissociation rate calculated in step b) is differing by more than 10% for the monomeric antibody and the dimeric, trimeric, tetrameric and/or oligomeric antibody.

One aspect as reported herein is an assay or method for determining the influence of antigen oligomerization on the pH-dependent binding of a (monoclonal) antibody to its antigen, wherein the method comprises the following steps:

a) capturing/immobilizing at a first pH-value the antibody on a solid phase to which the monomeric antigen of the antibody has been conjugated, i.e. the capturing/immobilization is by interaction of the antibody with its antigen, b) applying a pH-gradient from the first pH-value to a second pH-value to the solid phase, monitoring the dissociation of the antibody from the solid phase, and calculating a dissociation rate therefore, c) repeating steps a) to b) with the dimeric, trimeric, tetrameric and/or oligomeric antigen immobilized on the solid phase, wherein the pH-dependent binding of the antibody to its antigen is influenced by oligomerization if the dissociation rate calculated in step b) is differing by more than 10% for the monomeric antigen and the dimeric, trimeric, tetrameric and/or oligomeric antigen.

One aspect as reported herein is a method for separating or isolating a low-pH-binding (monoclonal) antibody from a mixture of antibodies binding to the same antigen, wherein the method comprises the following steps:

a) applying at a first pH-value the mixture of antibodies to a solid phase to which the antigen of the mixture of antibodies has been conjugated, i.e. capturing/immobilization the antibodies by interaction with its antigen, b) applying a pH-gradient from the first pH-value to a second pH-value to the solid phase and optionally monitoring the dissociation of the antibodies from the solid phase, c) collecting the antibody dissociating at a low pH-value, thereby separating or isolating a low-pH-binding (monoclonal) antibody from a mixture of antibodies binding to the same antigen.

In one embodiment, the low pH value is pH 6.5 or lower. In one embodiment, the low pH value is pH 6.0 or lower. In one embodiment, the low pH value is pH 5.5 or lower.

In the following embodiments of the previously outlined aspects are presented. It is understood that also all possible combinations of embodiments with each other are disclosed.

In one embodiment the conditions in step b) are kept constant except for the pH-value.

In one embodiment the method is a surface-plasmon-resonance method.

In one embodiment the dissociation is determined by surface plasmon resonance.

In one embodiment the solid phase is a surface plasmon resonance chip.

In one embodiment the antigen is immobilized at high density.

In one embodiment the solid phase is a surface plasmon resonance chip, the dissociation is determined by surface plasmon resonance and the antigen is immobilized at least at/with 500 RU to the surface plasmon resonance chip. In one preferred embodiment the antigen is immobilized at/with 500-4000 RU.

In one embodiment the binding of the antibody to the solid phase is an avid binding.

In one embodiment the first pH-value is pH 7.4 or higher, second pH-value is pH 5.5 or lower, or vice versa.

In one embodiment the antibody is monomeric if the antigen is not monomeric and vice versa.

In one embodiment the antibody is bivalent for its antigen.

In one embodiment dissociation is at a change of the binding signal of 5% or more.

In one embodiment dissociation is at a change of the binding signal of 10% or more.

In one embodiment the antigen is a soluble antigen.

In one embodiment the antibody is a monospecific antibody.

In one embodiment the antibody is a bispecific antibody.

In one embodiment the antibody is a bispecific antibody that has a first binding site specifically binding to a first epitope on the antigen and a second binding site specifically binding to a second epitope on the antigen.

In one embodiment the capturing is by injecting the antibody for 45 to 720 seconds, at a flow rate of 2.5 to 30 µL/min, in one preferred embodiment of 2.5 to 10 µL/min, and at a concentration of 0.6 µg/mL to 30 µg/mL. In one preferred embodiment the capturing is by injecting the antibody for about 60 seconds, at a flow rate of about 5 µL/min, and at a concentration of 0.6 µg/mL to 10 µg/mL.

In one embodiment the pH-gradient is for 100 to 10,000 seconds. In one embodiment the pH-gradient is for 1000 to 5000 seconds. In one embodiment the pH-gradient is for 2000-2300 seconds.

In one embodiment the dissociation pH-value is determined in a first step with a method according to the current invention.

In one embodiment the dissociation pH-value is maintained for 100 to 10,000 seconds. In one embodiment the dissociation pH-value is maintained from 150 to 1,000 seconds.

One aspect as reported herein is an assay or method for determining if the binding of a (monoclonal) antibody to its antigen is pH-dependent (pH-dependent antigen-binding), wherein the method comprises the following steps:

a) capturing/immobilizing at a first pH-value the antibody on a solid phase using a capture reagent specifically binding to a constant domain of the antibody, b) incubating the captured antibody with its antigen/applying to the captured antibody its antigen to form a captured antibody-antigen complex until a stable/constant binding signal is obtained, c) applying a pH-gradient from the first pH-value to a second pH-value to the solid phase and monitoring the dissociation of the antigen from the antibody, wherein the binding of the antibody to its antigen is pH-dependent if dissociation of the antigen from the antibody can be detected in step c).

One aspect as reported herein is an assay or method for selecting a (monoclonal) antibody that binds to its antigen pH-dependent (with pH-dependent antigen-binding), wherein the method comprises the following steps:

a) capturing/immobilizing at a first pH-value the antibody on a solid phase using a capture reagent specifically binding to a constant domain of the antibody, b) incubating the captured antibody with its antigen/applying to the captured antibody its antigen to form a captured antibody-antigen complex until a stable/constant binding signal is obtained, c) applying a pH-gradient from the first pH-value to a second pH-value to the solid phase and monitoring the dissociation of the antigen from the antibody, wherein the antibody is selected if dissociation of the antigen from the antibody can be detected in step c).

One aspect as reported herein is an assay or method for determining the pH-value at which an antibody that binds to its antigen pH-dependent dissociates from its antigen (pH-dependent dissociation), wherein the method comprises the following steps:

a) capturing/immobilizing at a first pH-value the antibody on a solid phase using a capture reagent specifically binding to a constant domain of the antibody, b) incubating the captured antibody with its antigen/applying to the captured antibody its antigen to form a captured antibody-antigen complex until a stable/constant binding signal is obtained, c) applying a pH-gradient from the first pH-value to a second pH-value to the solid phase and monitoring the dissociation of the antigen from the antibody, wherein the pH-value at which the antigen dissociates from the antibody is the pH-value of the pH-gradient at which dissociation of the antigen from the antibody can be detected in step c).

One aspect as reported herein is an assay or method for determining the dissociation rate constant $k_d$ of an antibody from its antigen, whereby the antibody binds to its antigen pH-dependent (pH-dependent dissociation), at the dissociation pH-value (the dissociation pH-values is the pH-value at which the dissociation of the antibody from its antigen can be detected), wherein the method comprises the following steps:

a) capturing/immobilizing at a first pH-value the antibody on a solid phase using a capture reagent specifically binding to a constant domain of the antibody, b) incubating the captured antibody with its antigen/applying to the captured antibody its antigen to form a captured antibody-antigen complex until a stable/constant binding signal is obtained, c) applying a pH-gradient from the first pH-value to the dissociation pH-value to the solid phase and thereafter maintaining the pH-value at said dissociation pH-value, d) recording the binding signal and calculating therefrom the dissociation rate constant $k_d$ and thereby determining the dissociation rate constant $k_d$ at the dissociation pH-value.

One aspect as reported herein is an assay or method for determining the influence of antibody oligomerization on the pH-dependent binding of a (monoclonal) antibody to its antigen, wherein the method comprises the following steps:

a) capturing/immobilizing at a first pH-value the monomeric antibody on a solid phase using a capture reagent specifically binding to a constant domain of the antibody, b) incubating the captured antibody with its antigen/applying to the captured antibody its antigen to form a captured antibody-antigen complex until a stable/constant binding signal is obtained, c) applying a pH-gradient from the first pH-value to a second pH-value to the solid phase, monitoring the dissociation of the antigen from the antibody, and calculating a dissociation rate therefore, d) repeating steps a) to c) with the dimeric, trimeric, tetrameric and/or oligomeric antibody, wherein the pH-dependent binding of the antibody to its antigen is influenced by oligomerization if the dissociation rate calculated in step c) is differing by more than 10% for the monomeric antibody and the dimeric, trimeric, tetrameric and/or oligomeric antibody.

One aspect as reported herein is an assay or method for determining the influence of antigen oligomerization on the pH-dependent binding of a (monoclonal) antibody to its antigen, wherein the method comprises the following steps:

a) capturing/immobilizing at a first pH-value the antibody on a solid phase using a capture reagent specifically binding to a constant domain of the antibody, b) incubating the captured antibody with its monomeric antigen/applying to the captured antibody its monomeric antigen to form a captured antibody-antigen complex until a stable/constant binding signal is obtained, c) applying a pH-gradient from the first pH-value to a second pH-value to the solid phase, monitoring the dissociation of the antigen from the antibody, and calculating a dissociation rate therefore, d) repeating steps a) to c) with the dimeric, trimeric, tetrameric and/or oligomeric antigen, wherein the pH-dependent binding of the antibody to its antigen is influenced by oligomerization if the dissociation rate calculated in step c) is differing by more than 10% for the monomeric antigen and the dimeric, trimeric, tetrameric and/or oligomeric antigen.

In the following embodiments of the previously outlined aspects are presented. It is understood that also all possible combinations of embodiments with each other are disclosed.

In one embodiment all conditions except for the pH-value are kept constant in step c).

In one embodiment the dissociation is determined by surface plasmon resonance.

In one embodiment the solid phase is a surface plasmon resonance chip.

In one embodiment the antibody is immobilized at high density.

In one embodiment the solid phase is a surface plasmon resonance chip, the dissociation is determined by surface plasmon resonance and the antibody is immobilized at least at/with 50 RU to the surface plasmon resonance chip. In one preferred embodiment the antibody is immobilized at/with 50-400 RU.

In one embodiment the first pH-value is pH 7.4 or higher, second pH-value is pH 5.5 or lower, or vice versa.

In one embodiment the antibody is monomeric if the antigen is not monomeric and vice versa.

In one embodiment the antibody is bivalent for its antigen.

In one embodiment dissociation is at a change of the binding signal of 5% or more.

In one embodiment dissociation is at a change of the binding signal of 10% or more.

In one embodiment the antigen is a soluble antigen.

In one embodiment the antibody is a monospecific antibody.

In one embodiment the antibody is a bispecific antibody.

In one embodiment the antibody is a bispecific antibody that has a first binding site specifically binding to a first epitope on the antigen and a second binding site specifically binding to a second epitope on the antigen.

In one embodiment the capturing is by injecting the antibody for 45 to 720 seconds, at a flow rate of 2.5 to 30 $\mu$L/min, in one preferred embodiment of 2.5 to 10 $\mu$L/min, and at a concentration of 0.6 $\mu$g/mL to 30 $\mu$g/mL. In one preferred embodiment the capturing is by injecting the antibody for about 60 seconds, at a flow rate of about 5 $\mu$L/min, and at a concentration of 0.6 $\mu$g/mL to 10 $\mu$g/mL.

In one embodiment the pH-gradient is for 100 to 10,000 seconds. In one embodiment the pH-gradient is for 1000 to 5000 seconds. In one embodiment the pH-gradient is for 2000-2300 seconds.

In one embodiment the dissociation pH-value is determined in a first step with a method according to the current invention.

In one embodiment the dissociation pH-value is maintained for 100 to 10,000 seconds. In one embodiment the dissociation pH-value is maintained from 150 to 1,000 seconds.

DETAILED DESCRIPTION OF THE INVENTION

Definitions

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "antibody" herein is used in the broadest sense and encompasses various antibody structures, including but not limited to monoclonal antibodies, multispecific antibodies (e.g. bispecific antibodies, trispecific antibodies), and antibody fragments so long as they exhibit the desired antigen-binding activity.

An antibody in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (Fc$\gamma$R), such as phagocytic cells, or ii) to cells bearing the neonatal Fc receptor (FcRn) also known as Brambell receptor. It also mediates the binding to some factors including factors of the classical complement system such as component (C1q). The constant domains of an antibody heavy chain comprise the CH1-domain, the CH2-domain and the CH3-domain, whereas the light chain comprises only one constant domain, CL, which can be of the kappa isotype or the lambda isotype.

The variable domain of an immunoglobulin's light or heavy chain in turn comprises different segments, i.e. four framework regions (FR) and three hypervariable regions (HVR).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "binding to" denotes the binding of a binding site to its target, such as e.g. of an antibody binding site comprising an antibody heavy chain variable domain and an antibody light chain variable domain (VH/VL-pair) to the respective antigen. This binding can be determined using, for example, a BIAcore® assay (GE Healthcare, Uppsala, Sweden).

For example, in one possible embodiment of the BIAcore® assay the antigen is bound to a surface and binding of the antibody binding site is measured by surface plasmon resonance (SPR). The affinity of the binding is defined by the terms ka (association constant: rate constant for the association to form a complex), kd (dissociation constant; rate constant for the dissociation of the complex), and $K_D$ ($k_d/k_a$). Alternatively, the binding signal of a SPR sensorgram can be compared directly to the response signal of a reference, with respect to the resonance signal height and the dissociation behaviors.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein are in one preferred embodiment "bivalent".

In certain embodiments, the antibody is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, multispecific antibodies may bind to two different epitopes of the same antigen. Multispecific antibodies may also be used to localize cytotoxic agents to cells, which express the antigen. Multispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (scFv) dimers (see, e.g., Gruber, M., et al., J. Immunol. 152 (1994) 5368-5374); and preparing trispecific antibodies as described, e.g., in Tutt, A., et al., J. Immunol. 147 (1991) 60-69).

The antibody or fragment can also be a multispecific antibody as described in WO 2009/080251, WO 2009/080252, WO 2009/080253, WO 2009/080254, WO 2010/112193, WO 2010/115589, WO 2010/136172, WO 2010/145792, or WO 2010/145793.

The antibody or fragment thereof may also be a multispecific antibody as disclosed in WO 2012/163520.

The Method as Reported Herein

The increasing complexity of novel biotherapeutics such as antibodies raises new challenges for functional characterization. This is especially true, if antibodies have to be characterized that show a pH-dependent binding to their respective antigen.

Exemplary antibodies with pH-dependent antigen-binding and their generation is reported, e.g., in EP 2 275 443. A pH-dependent antigen-binding can be introduced in principle in any antibody. By introducing a pH-dependent antigen-binding into an antibody a single antigen-binding antibody can be converted into a repeatedly antigen-binding antibody, capable of binding to multiple antigen molecules. When an antibody binds to multiple antigen molecules such an antibody exerts more superior in vivo effects than those of ordinary antigen-binding molecules.

The methods for impairing the antigen-binding activity of an antibody at pH 5.8 as compared to that at pH 7.4 (methods for conferring the pH-dependent binding ability) are not particularly limited and may be any methods. Such methods include, for example, methods for impairing the antigen-binding activity at pH 5.8 as compared to that at pH 7.4 by substituting histidine for other amino acids in the antibody or inserting histidine into the antibody. It is already known that an antibody can be conferred with a pH-dependent antigen-binding activity by substituting histidine for amino acids in the antibody (FEBS Letter, 309(1), 8588 (1992)). Such histidine mutation (substitution) or insertion sites are not particularly limited, and any site is acceptable as long as the antigen-binding activity at pH 5.8 is lowered than that at pH 7.4 (the value of $K_D$(pH5.8)/$K_D$(pH7.4) gets greater) as compared to before mutation or insertion. In case of an antibody, such sites include, for example, sites within an antibody, variable region. The appropriate number of histidine mutation or insertion sites can be appropriately determined by those skilled in the art.

Histidine may be substituted or inserted at a single site, or two or more sites. It is also possible to introduce non-histidine mutation (mutation with amino acids other than histidine) at the same time. Furthermore, histidine mutation may be introduced simultaneously with histidine insertion. It is possible to substitute or insert histidine at random using a method such as histidine scanning, which uses histidine instead of alanine in alanine scanning known to those skilled in the art. Alternatively, antigen-binding molecules whose $K_D(\text{pH}5.8)/K_D(\text{pH}7.4)$ is increased as compared to before mutation can be selected from an antigen-binding molecule library with random histidine mutation or insertion.

When histidine is substituted for amino acids of an antibody or inserted between amino acids of the antibody, it is preferred, but not required, that the antigen-binding activity of the antibody at pH 7.4 after histidine substitution or insertion is comparable to that at pH 7.4 before histidine substitution or insertion. The "antigen-binding activity of the antibody at pH 7.4 after histidine substitution or insertion is comparable to that at pH 7.4 before histidine substitution or insertion" means that even after histidine substitution or insertion, the antibody retains 10% or more, preferably 50% or more, more preferably 80% or more, and still more preferably 90% or more of the antigen-binding activity of before histidine substitution or insertion. When the antigen-binding activity of the antibody has been impaired due to histidine substitution or insertion, the antigen-binding activity may be adjusted by introducing substitution, deletion, addition, and/or insertion of one or more amino acids into the antibody so that the antigen-binding activity becomes comparable to that before histidine substitution or insertion.

Alternative methods for impairing the antigen-binding activity of an antibody at pH 5.8 as compared to that at pH 7.4 include methods of substituting non-natural amino acids for amino acids in an antibody or inserting non-natural amino acids into amino acids of an antibody. It is known that the pKa can be artificially controlled using non-natural amino acids (Angew. Chem. Int. Ed. 2005, 44, 34; Chem. Soc. Rev. 2004 Sep. 10; 33(7):422-30; Amino Acids. 1999; 16(3-4):345-79). Thus, non-natural amino acids can be used instead of histidine described above. Such non-natural amino acid substitution and/or insertion may be introduced simultaneously with the histidine substitution and/or insertion described above. Any non-natural amino acids may be used in the present invention. It is possible to use non-natural amino acids known to those skilled in the art.

Accordingly, an objective of the present invention is to provide methods for determining the pH-dependent antigen-binding of antibodies that bind their antigens multiple times.

Standard SPR-based assay setups have been described in the art. These allow to assess the binding activity of an antibody to its antigen(s) at one set of conditions.

In the present invention, the absolute difference in the antigen-binding activity between acidic and neutral pH is not essential as long as the antigen-binding activity at acidic pH is different from that at neutral pH.

However, in one embodiment the value of $K_D(\text{pH}5.8)/K_D(\text{pH}7.4)$, which is a ratio of dissociation constant $(K_D)$ against an antigen at pH 5.8 and that at pH 7.4, is preferably 2 or greater, more preferably 10 or greater, and still more preferably 40 or greater. The upper limit of $K_D(\text{pH}5.8)/K_D(\text{pH}7.4)$ value is not particularly limited, and may be any value, for example, 400, 1,000, or 10,000, as long as the molecule can be produced by technologies of those skilled in the art.

However, in one embodiment the value of $K_D(\text{pH}7.4)/K_D(\text{pH}5.8)$, which is a ratio of dissociation constant $(K_D)$ against an antigen at pH 7.4 and that at pH 5.8, is preferably 2 or greater, more preferably 10 or greater, and still more preferably 40 or greater. The upper limit of $K_D(\text{pH}7.4)/K_D(\text{pH}5.8)$ value is not particularly limited, and may be any value, for example, 400, 1,000, or 10,000, as long as the molecule can be produced by technologies of those skilled in the art.

When the antigen is a soluble antigen, the antigen-binding activity can be presented in terms of the dissociation constant $(K_D)$. Alternatively, when the antigen is a membrane antigen, the antigen-binding activity can be presented in terms of the apparent dissociation constant. The dissociation constant $(K_D)$ and apparent dissociation constant (apparent $K_D$) can be determined by methods known to those skilled in the art, for example, using BIAcore (GE healthcare), Scatchard plot, or FACS.

In one embodiment when the dissociation rate constant $(k_d)$ is used as an indicator for the difference in the binding activity instead of the dissociation constant $(K_D)$, the value of $k_d(\text{pH}5.8)/k_d(\text{pH}7.4)$, which is a ratio of dissociation rate constant $(k_d)$ against an antigen at pH 5.8 and that at pH 7.4, is preferably 2 or greater, more preferably 5 or greater, even more preferably 10 or greater, and still more preferably 30 or greater. The upper limit of $k_d(\text{pH}5.8)/k_d(\text{pH}7.4)$ value is not particularly limited, and may be any value, for example, 50, 100, or 200, as long as the molecule can be produced by technologies common to those skilled in the art.

In one embodiment when the dissociation rate constant (kd) is used as an indicator for the difference in the binding activity instead of the dissociation constant (KD), the value of kd(pH7.4)/kd(pH5.8), which is a ratio of dissociation rate constant (kd) against an antigen at pH 7.4 and that at pH 5.8, is preferably 2 or greater, more preferably 5 or greater, even more preferably 10 or greater, and still more preferably 30 or greater. The upper limit of kd(pH7.4)/kd(pH5.8) value is not particularly limited, and may be any value, for example, 50, 100, or 200, as long as the molecule can be produced by technologies common to those skilled in the art.

When the antigen is a soluble antigen, the antigen-binding activity can be presented in terms of the dissociation rate constant $(k_d)$. Alternatively, when the antigen is a membrane antigen, the antigen-binding activity can be presented in terms of the apparent dissociation rate constant (apparent kd). The dissociation rate constant $(k_d)$ and apparent dissociation rate constant (apparent $k_d$) can be determined by methods according to the current invention directly at the dissociation pH-value.

Herein, impairing the antigen-binding activity at acidic pH as compared to that at neutral pH means that the antigen-binding ability of an antibody at pH 4.0 to pH 6.5 is impaired as compared to that at pH 6.7 to pH 10.0, preferably that the antigen-binding activity of an antibody at pH 5.5 to pH 6.5 is impaired as compared to that at pH 7.0 to pH 8.0, and more preferably that the antigen-binding activity of an antibody at pH 5.8 is impaired as compared to that at pH 7.4. Accordingly, in the present invention, acidic pH is typically pH 4.0 to pH 6.5, preferably pH 5.5 to pH 6.5, and more preferably pH 5.8. Alternatively, in the present invention, neutral pH is typically pH 6.7 to pH 10.0, preferably pH 7.0 to pH 8.0, and more preferably pH 7.4.

Thus, in one embodiment the first pH-value is between and including pH 6.7 to pH 10.0 and the second pH-value is between and including pH 4.0 to pH 6.5. In one embodiment the first pH-value is between and including pH 7.0 to pH 8.0 and the second pH-value is between and including pH 5.5 to pH 6.5. In one embodiment the first pH-value is between and including pH 7.2 to pH 7.6 and the second pH-value is between and including pH 5.5 to pH 5.8. In one preferred embodiment the first pH-value is about pH 7.4 and the second pH-value is between and including pH 5.5 to pH 5.8.

The current invention is based, at least in part, on the finding that a surface plasmon resonance experiment can be performed with a pH-gradient. Thereby it is possible to characterize the pH-dependent antigen-binding of antibodies on the one hand by determining the exact pH-value at which this dissociation of the antibody from its antigen takes place, i.e. the dissociation pH-value, and on the other hand by determining the dissociation rate constant at said dissociation pH-value.

The methods according to the current invention comprise as essential step the recording or monitoring of the binding signal of antibody to antigen while a pH-gradient is applied. At the point of the pH-gradient at which binding signal starts to decrease the interaction between the antibody and its antigen is weakened due to protonation or deprotonation of amino acid residues in the binding site. Said point of the pH-gradient defines the dissociation pH-value for the pH-dependent interaction between the antibody and its antigen.

For example, in order to assess the suitability of an antibody with pH-dependent antigen-binding as repeatedly antigen-binding antibody capable of binding to multiple antigen molecules the pH-dependent antigen-binding can be determined with a method according to the invention. If the binding at lysosomal pH, i.e. below pH 6.0, preferably at about pH 5.0, to the antigen is reduced (or even eliminated) while binding at physiological pH, i.e. above pH 7.0, preferably at about pH 7.4, is maintained (or even maximal) said antibody is suitable for the intended purpose.

Thus, the methods according to the current invention comprise the central step of exposing an antibody-antigen-complex to a pH gradient from physiological pH to lysosomal pH and determining i) if at all, or ii) the precise pH-value at which the antibody-antigen-complex dissociates.

Even though the above has been outlined for a pH-gradient from neutral to acidic pH-value the methods according to the current invention can be used with any pH-gradient, i.e. from neutral to acidic or from neutral to alkaline or from alkaline to acidic or from acidic to alkaline.

Thus, one aspect as reported herein is an assay or method for determining if the binding of a (monoclonal) antibody to its antigen is pH-dependent (pH-dependent antigen-binding), wherein the method comprises the following steps:

a) capturing/immobilizing at a first pH-value the antibody on a solid phase to which the antigen of the antibody has been conjugated, b) applying a pH-gradient from the first pH-value to a second pH-value to the solid phase and monitoring the dissociation of the antibody from the solid phase, wherein the binding of the antibody to its antigen is pH-dependent if dissociation of the antibody from the solid phase can be detected in step b).

One aspect as reported herein is an assay or method for determining the dissociation rate constant $k_d$ of an antibody from its antigen, whereby the antibody binds to its antigen pH-dependent (pH-dependent dissociation), at the dissociation pH-value (the dissociation pH-values is the pH-value at which the dissociation of the antibody from its antigen can be detected), wherein the method comprises the following steps:

a) capturing/immobilizing at a first pH-value the antibody on a solid phase using a capture reagent specifically binding to a constant domain of the antibody, b) incubating the captured antibody with its antigen to form a captured antibody-antigen complex until a stable/constant binding signal is obtained, c) applying a pH-gradient from the first pH-value to the dissociation pH-value to the solid phase and thereafter maintaining the pH-value at said dissociation pH-value, d) recording the binding signal and calculating therefrom the dissociation rate constant $k_d$ and thereby determining the dissociation rate constant $k_d$ at the dissociation pH-value.

This approach is advantageous as by lowing the pH-value from above the dissociation pH-value to the dissociation pH-value the process during endocytosis and lysosomal acidification can be simulated. Additionally, the starting point for the determination of the dissociation rate constant can be precisely set allowing for a more accurate determination of said dissociation rate constant at the dissociation pH-value.

REFERENCE LIST

[1] M. A. Cooper, Nature Reviews Drug Discovery 1, (2002) 515-528.

[2] D. G. Myszka, Journal of Molecular Recognition 12, (1999) 390-408.

[3] R. L. Rich, D. G. Myszka, Journal of Molecular Recognition 13, (2000) 388-407.

[4] D. G. Myszka, R. L. Rich, Pharmaceutical science & technology today 3, (2000) 310-317.

[5] R. Karlsson, A. Faelt, Journal of immunological methods 200, (1997) 121-133.

[6] T. A. Morton, D. G. Myszka, Methods in enzymology 295, (1998) 268-294.

[7] K. Nagata, H. Handa, Real-time analysis of biomolecular interactions, Springer, 2000.

[8] R. L. Rich, D. G. Myszka, Current opinion in biotechnology 11, (2000) 54-61.

[9] A. C. Malmborg, C. A. Borrebaeck, Journal of immunological methods 183, (1995) 7-13.

[10] W. Huber, F. Mueller, Current pharmaceutical design 12, (2006) 3999-4021.

[11] C. Gassner, F. Lipsmeier, P. Metzger, H. Beck, A. Schnueriger, J. T. Regula, J. Moelleken, Journal of pharmaceutical and biomedical analysis 102, (2015) 144-149.

The following examples and figures are provided to aid the understanding of the present invention, the true scope of which is set forth in the appended claims. It is understood that modifications can be made in the procedures set forth without departing from the spirit of the invention.

EXAMPLES

Equipment and Reagents

Figure 1:
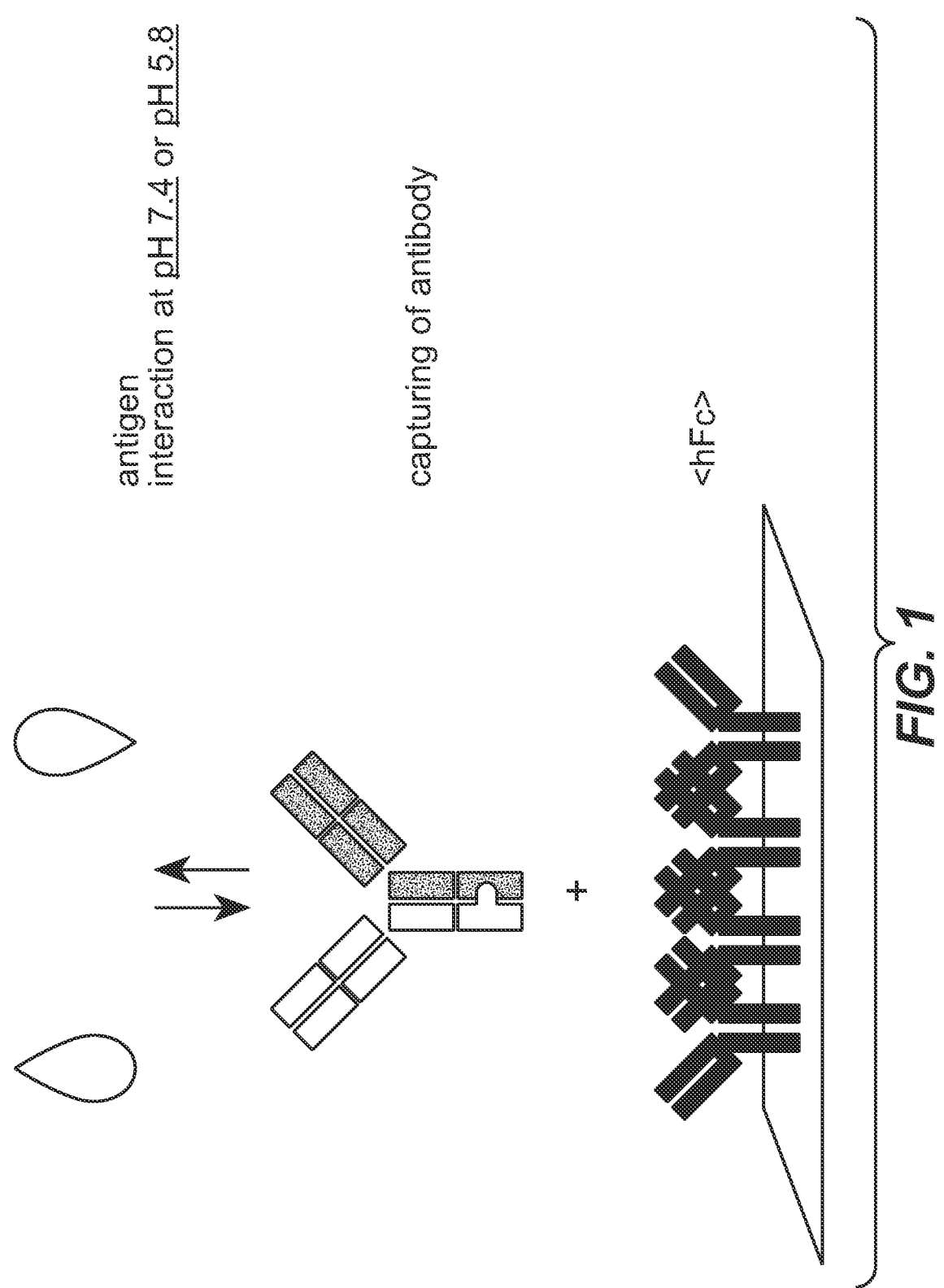
FIG. 1 Scheme of classic SPR-BIAcore kinetic experiment wherein only one constant buffer conditions for one measurement is applied.
Figure 2:
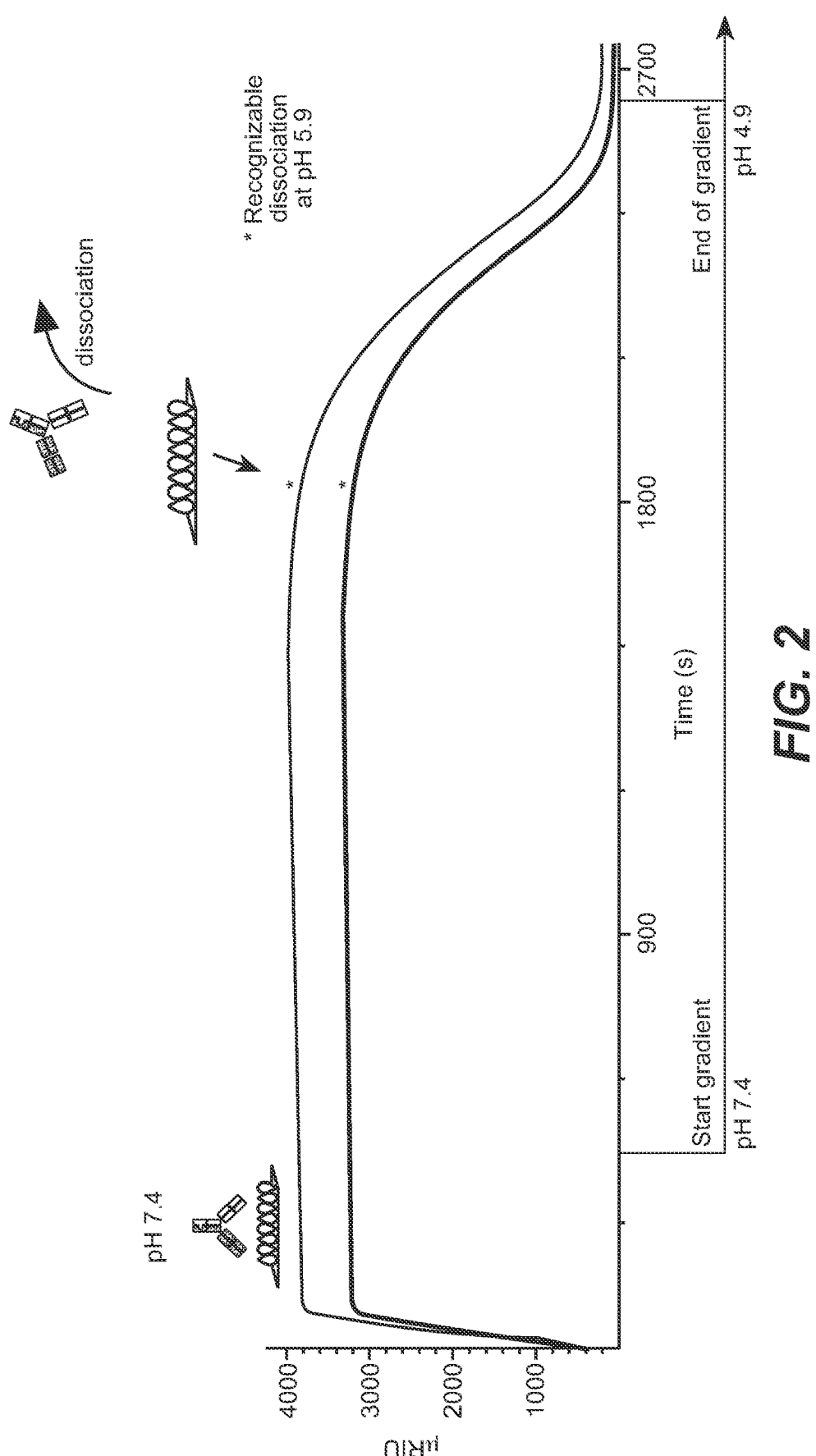
FIG. 2 Exemplary sensogram for pH-dependent antibody dissociation from a solid surface according to the method of the invention with a pH-gradient from pH 7.4 to pH 4.9.
Figure 3:
FIG. 3 Exemplary sensogram for determination of the dissociation rate constant at the dissociation pH-value.

All SPR experiments were performed on a Xantec SR7500DC with sensor chip Xantec SCR CMD500L

Example 1

Chip Preparation

For the immobilization of the antigen two flow cells (Fc) have been prepared, Fc1 as a blank control and Fc2 as specific target binding interaction surface. For antigen immobilization on Flow cell two the surface has been activated by EDC/NHS to prepare the amine coupling of a dimeric antigen construct. The antigen dimer has been prepared in a 10 mM acetate buffer at pH 4.5 in a concentration of 30µg/ml. This solution was injected over Fc2 for 10 min by a flow rate of 20µl/min Running the pH Gradient To establish the gradient two PBS-P+ buffers were prepared. Buffer A has been set to a pH of 7.4. Buffer B has been set to pH 4.9.

At a flow rate of 100 µl/min the antibody samples were injected in a concentration of 100 nM for 90 seconds in Buffer A. After 210 seconds of equilibration the gradient started from 100% buffer A to 100% buffer B within 2400 seconds. In the end of the run the surface was regenerated by a 10 mM glycine buffer at a pH of 1.5.

The pH value at start of dissociation of the pH-dependent binders was determined by the ratio of buffer A and buffer B of 25:75. Measuring this mixture resulted in a pH value of 5.85 to 5.9.

Example 2

Chip Preparation

For the immobilization of the anti-human Fc capture antibody (<hFc>GE BR-1008-39) two flow cells have been prepared, Fc1 as a blank control and Fc2 as specific target binding interaction surface. For the capture antibody immobilization on Flow cell two the surface has been activated by EDC/NHS to prepare the amine coupling. <hFc> has been prepared in a 10 mM acetate buffer at pH 4.5 in a concentration of 30µg/ml. This solution was injected over Fc2 for 10 min by a flow rate of 20 µl/min.

Running the pH Gradient after Antibody

To establish the gradient two PBS-P+ buffers were prepared. Buffer A has been set to a pH of 7.4. Buffer B has been set to pH 4.9. At a flow rate of 100 µl/min the antibody in question was injected in a concentration of 100 nM for 90 seconds in Buffer A. In a second step different antigen preparations (dimer, wildtype and monomer) were injected at a concentration of 100 nM in buffer A for 90 seconds. After 210 seconds of equilibration the gradient started from 100% buffer A to 100% buffer B within 2400 seconds. In the end of the run the surface was regenerated by a 3 M $MgCl_2$ solution.

The invention claimed is:

1. A surface plasmon resonance method for determining a dissociation rate constant $k_d$ of an antibody from its antigen at the dissociation pH-value, wherein the method comprises the following steps:

a) immobilizing at a first pH-value the antibody on a solid phase using an anti-Fc capture antibody as a capture reagent, b) incubating the immobilized antibody with its antigen to form a captured antibody-antigen complex, c) applying a pH-gradient from the first pH-value to a second pH-value to the solid phase to determine the dissociation pH-value of the antigen from the antibody and thereafter maintaining the pH-value at said dissociation pH-value, and d) recording the binding signal during the maintaining of the pH-value and calculating therefrom the dissociation rate constant $k_d$ of the antibody from its antigen at the dissociation pH-value;

wherein the first pH-value is about 7.4 and the second pH-value is between and including pH 4.0 to pH 6.5.

2. The method according to claim 1, wherein the dissociation is determined by surface plasmon resonance.

3. The method according to claim 1, wherein the antigen is immobilized at high density.

4. The method according to claim 1, wherein the dissociation pH-value occurs at a change of the binding signal of 5% or more.

5. The method according to claim 1, wherein the antigen is a soluble antigen.

6. The method according to claim 1, wherein the antibody is a monospecific antibody.

7. The method according to claim 1, wherein the immobilizing is by injecting the antibody for 45 to 720 seconds, at a flow rate of 2.5 to 30 µL/min, and at a concentration of 0.6 µg/mL to 30 µg/mL.

\* \* \* \* \*